(12) United States Patent
Shinomiya et al.

(10) Patent No.: US 6,887,272 B2
(45) Date of Patent: May 3, 2005

(54) ARTIFICIAL PYRAMID

(75) Inventors: Kenichi Shinomiya, Tokyo (JP); Soichiro Itoh, Tokyo (JP); Junzo Tanaka, Ibaraki (JP); Masanori Kikuchi, Ibaraki (JP)

(73) Assignees: Japan Science and Technology Agency, Kawaguchi (JP); National Institute for Materials, Tsukuba (JP)

( * ) Notice: Subject to any disclaimer, the term of this patent is extended or adjusted under 35 U.S.C. 154(b) by 99 days.

(21) Appl. No.: 10/468,010

(22) PCT Filed: Feb. 20, 2002

(86) PCT No.: PCT/JP02/01508
§ 371 (c)(1),
(2), (4) Date: Dec. 22, 2003

(87) PCT Pub. No.: WO02/065955
PCT Pub. Date: Aug. 29, 2002

(65) Prior Publication Data
US 2004/0082998 A1 Apr. 29, 2004

(30) Foreign Application Priority Data
Feb. 23, 2001 (JP) ......................................... 2001-049493

(51) Int. Cl.[7] ............................. A61F 2/28; A61F 13/00
(52) U.S. Cl. ................................. 623/17.11; 623/16.11; 623/23.51; 623/23.56; 623/23.61
(58) Field of Search ................ 623/16.11, 17.11–17.16, 623/23.61, 23.56, 23.51; 423/308; 424/422–424

(56) References Cited

U.S. PATENT DOCUMENTS 3,929,971 A * 12/1975 Roy ............................ 423/308
4,904,261 A * 2/1990 Dove et al. .................... 623/17
5,320,844 A * 6/1994 Liu ............................ 424/422
5,492,697 A * 2/1996 Boyan et al. ............. 623/16.11
5,702,449 A * 12/1997 McKay ........................ 623/17
5,776,199 A * 7/1998 Michelson ................... 623/17

FOREIGN PATENT DOCUMENTS

DE 3741493 * 6/1989
JP 3-29663 * 2/1991

(Continued)

OTHER PUBLICATIONS

Junzo Tanaka et al.; *Synthesis of Collagen and Inorganic Material Composite;* Surface Science vol. 20, No. 9, pp. 600–606, 1999 (Cited in Int'l Preliminart Examination Report).*

(Continued)

*Primary Examiner*—David J. Isabella
(74) *Attorney, Agent, or Firm*—Westerman, Hattori, Daniels & Adrian, LLP

(57) ABSTRACT

Disclosed is an artificial vertebra having a bone-marrow regenerating function, comprising a hydroxyapatite (HAp)/collagen (Col) composite body formed by pressure-dehydrating a coprecipitate of hydroxyapatite and collagen to have a nanocomposite structure in which HAp particles are conjugated along a Col fiber while aligned each of the c-axes of the HAp particles along the Col fiber. The HAp/Col composite body is formed with a perforated aperture for allowing a blood vessel and an osteogenic cell to intrude thereinto. The present invention also provides a biodecomposable/bioabsorbable support for fixing an artificial vertebra, comprising a polylactic acid plate prepared by injection-molding molten polylactic acid and then extrusion-molding the injection-molded polylactic acid in such a manner that it is draw-oriented in a uniaxial direction. The plate has four corner regions each formed with a screw hole for fixing the plate to vertebral bodies.

8 Claims, 5 Drawing Sheets

FOREIGN PATENT DOCUMENTS

| | | | |
|---|---|---|---|
| JP | 4-303444 | * | 10/1992 |
| JP | 5-168647 | * | 7/1993 |
| JP | 7-88174 | * | 4/1995 |
| JP | 7-101708 | * | 4/1995 |
| JP | 8-336584 | * | 12/1996 |
| JP | 10-33656 | * | 2/1998 |
| JP | 11-199209 | * | 7/1999 |
| JP | 11-513590 | * | 11/1999 |
| JP | 2000-517221 | * | 12/2000 |
| WO | WO 98/09586 | * | 3/1998 |
| WO | WO 98/17209 | * | 4/1998 |
| WO | WO 98/17330 | * | 4/1998 |
| WO | WO 99/44529 | * | 9/1999 |

OTHER PUBLICATIONS

Nanzando Medical Dictionary, "Havarsian canal"(p.1656), "Volkmann's canal" (p. 1812), 1998 (Cited in Int'l Preliminary Examination Report).*

Soichiro Itoh et al.; *The biocompatibility and osteoconductive activity of a novel hydroxyapatite/collage composite biomaterial, and its function as a carrier of rhBMP–2;* J. Biomedicals Research 54, pp. 445–453, Dec. 4, 2000 (Discussed in spec. p. 2).*

* cited by examiner

ARTIFICIAL PYRAMID

TECHNICAL FIELD

The present invention relates to an artificial vertebra. In particular, the present invention relates to an artificial vertebra having a bone-marrow regenerating function which is achieved by using a hydroxyapatite/collagen (HAp/Col) composite material capable of self-organizing after filled in a bone defect area of a vertebral body in anterior fusion of the spine, and a support composed of a polylactic-acid (poly-L-lactide: PLLA) plate suitable for fixing the artificial vertebra to the vertebral body.

BACKGROUND ART

Generally, if an artificial material is implanted to fill a bone defect area in a living body, it will be wrapped by a fibrous membrane, and finally isolated from surrounding tissues. This phenomenon is caused by a biological reaction for self-protecting from foreign matters. Exceptionally, some materials can be joined directly to a surrounding bone without any formation of fibrous membranes. A typical material having such a property includes hydroxyapatite $Ca_{10}(PO_4)_6(OH)_2$ and tricalcium phosphate $Ca_3(PO_4)_2$.

Recently, an artificial bone made of an organic/inorganic composite material based on the above bioceramics is being developed. For example, Japanese Patent Laid-Open Publication No. H07-101708 discloses an implant for artificial bones or artificial tooth roots, which is formed as a molded piece by adding 5 to 40 weight % of water to a composition powder containing an apatite powder having a crystal grain size of 0.5 μm or less and a biomolecular organic matter such as collagen and applying a pressure of 50 MPa or more to the composition powder maintained at a temperature of 0 to 200° C., wherein the Young's modulus of the implant is adjustable in the range of 2 GPa to 110 MPa.

The inventors developed an oriented apatite/collagen composite material excellent in flexural strength, Young's modulus and compressive strength suitable as a biomedical bone-replaceable bone-reconstruction material having a bone-induction ability and a bone-conduction ability, through a method in which a phosphoric-acid solution containing collagen and a solution containing calcium salt are simultaneously dropped into a reaction vessel to coprecipitate calcium phosphate and collagen, and the obtained precipitate is shaped under pressure (Japanese Patent Laid-Open Publication No. H11-199209, J. BIOMEDICALS RESEARCH, 54: 445–453, Published online, 4 Dec. 2000).

Japanese Patent Laid-Open Publication No. H08-336584 discloses an apatite porous body for artificial bone marrows, which includes 30 weight % or more of apatite crystal particles having a particle size of 2 nm to 0.2 μm and an organic matter such as collagen, and has a through-hole with a diameter of 10 μm to 2 mm. Japanese Patent Laid-Open Publication No. H07-88174 discloses a compression-molded osteogenic implant comprising rhBPM (Bone Morphogenetic Protein) and a carrier therefor, wherein the osteogenic implant is formed in a support made of a bioceramics material.

As a substitute for a conventional bone-connecting metal plate or screw which has been generally used to fix, aid and restore a broken bone, a fusion-molded or extrusion-molded body made of polylactic acid as a biodecomposable/bioabsorbable material and formed in a rod, plate, screw or pin shape (Japanese Patent Laid-Open Publication Nos. H03-29663 and H05-168647).

While an autologous bone has been extracted and used as an implant for filling a bone defect area of a vertebral body in many cases, various kinds of artificial implants made of metal or ceramic have also been developed.

Since a vertical load is imposed on an artificial implant during use, the artificial implant must adequately satisfy requirements of flexural strength, flexural modulus and compressive strength, and have characteristics equivalent to those of an autologous bone.

For example, Japanese Patent Laid-Open Publication No. H04-303444 (Publication-1) discloses an artificial intervertebral disk in block form having various shapes. The artificial intervertebral disk comprises a plurality of porous bodies made of metal or ceramic, and a block made of polyvinyl alcohol hydrogel and integrally disposed between the porous bodies.

The specification and drawings of U.S. Pat. No. 5,702,449 (Publication-2) discloses an artificial vertebra comprising a load support member composed of a cylindrical metal sleeve with a sidewall having a number of apertures, and a bioceramic, such as hydroxyapatite/tricalcium phosphate, received in the inner space of the support member.

Japanese Patent Laid-Open Publication No. H10-33656 (Publication-3) discloses a vertebral-body fusion member in block form having various shapes. The vertebral-body fusion member comprises a porous body and a dense body having a mechanical strength which are made of β-tricalcium phosphate (TCP) as a bioabsorbable material having a bone-conduction ability, wherein the porous and dense bodies are integrally combined so that the dense body maintains an initial strength, and the porous body is gradually transformed into an autologous bone.

Japanese Patent Laid-Open Publication No. H11-513590 (Publication-4) discloses a porous biodecomposable matrix for bone replacement in spinal fusion, filling of bone defects, repair of broken bones or filling of periodontal defects. The matrix includes a network of insoluble biopolymer fiber (fibril collagen), binder, and fixed calcium phosphate mineral (hydroxyapatite) which are linked together. Publication-4 also discloses that it is desired to arrange the weight ratio of collagen to calcium phosphate mineral in the range of 8:2 to 1:1, to cross-link the matrix with glutalaldehyde or the like, and to include a bone marrow cell, an autologous bone and a bone growth factor.

Published Japanese Translation of PCT International Publication for Patent Application No. 2000-507484 (Publication-5) discloses a vertebral-column spacer comprising a load support member which includes a bone implant having a bioceramics matrix and a bone-growth stimulating component impregnated in the bioceramics matrix Published Japanese Translation of PCT International Publication for Patent Application No. 2000-508221 (Publication-6) discloses a cylindrical implant comprising a matrix body which has fine pores and includes a biphasic calcium phosphate ceramic containing 2 to 40 volume % of hydroxyapatite (HAp) and 98 to 60 volume % of tricalcium phosphate (TCp), and a bone-growth inducing factor (TGF-β, BMP, prostaglandin etc.) captured in the matrix body. Publication-6 also discloses that the ceramic has fine pores with a size of about 200 to 600 μm, and the porosity rate of the ceramic is in the range of about 60 to 80%.

Published Japanese Translation of PCT International Publication for Patent Application No. 2000-517221 (Publication-7) discloses a prismatic or cylindrical intervertebral implant made of a conventional ceramic material having a maximum porosity of 30 volume %, wherein each of pores with a diameter of less than 100 μm is filled with air. Publication-7 also discloses that the intervertebral implant has a compressive strength of 400 to 600 MPa, and the ceramic material is transparent to X-ray.

The block disclosed in Publication-1 is simply implanted in a cortical bone, but no bone-marrow structure will be formed. The artificial vertebra disclosed in Publication-2 has a problem of causing rupture on the boundary between the bone and the implant under repetitive stress due to remanence of the metal sleeve which originally has no potential of becoming bone. Further, there is the risk of causing disruption of the implant itself due to early absorption/deprivation of TCP, and poor bone conduction ability provided only by HA left at the central region of the sleeve.

Publication-3 simply discloses that the dense body is combined with the porous body to compensate for a poor strength of β-tricalcium phosphate (TCP). The matrix disclosed in Publication-4 simply includes a mixture of collagen and apatite, which has neither a bone-like nanocomposite structure nor a self-organizing function. In addition, the matrix is insufficient in strength and bone-forming ability.

The matrix itself of the spacer disclosed in Publication-5 has no ability of forming bone marrow. The spacer also involves a conventional problem such as complications in a bone-extraction area and metal fatigue, due to use of an autologous bone and a metal component. Further, allogeneic bone transplantation involves the risk of AIDS or hepatitis infection. While the porous body disclosed in Publication-6 is made of a TCP-HAp composite material, it has no self-organizing function. Further, the implant itself is not a carrier directly absorbing BMP. While the porous body disclosed in Publication-7 has a high porosity, it involves the risk of rupture under repetitive stress due to insufficient transformation into an autologous bone. Further, any vertebra structure cannot be biologically formed without using a bone-marrow implant.

As mentioned above, each of the conventional artificial vertebrae is not a bioabsorbable material having abilities of bone-marrow formation and self-organization (bone-tissue regeneration).

DISCLOSURE OF THE INVENTION

It is therefore an object of the present invention to provide an artificial vertebra with a 3-dimensional structure, having a microstructure (nanocomposite structure) and composition equivalent to those of an autologous bone, and exhibiting excellent characteristics such as invasivity of new blood vessels, osteogenic cells and others.

The inventors developed a HAp/Col composite material excellent in bone-conduction ability, as disclosed in the aforementioned Japanese Patent Laid-Open Publication No. H11-199209, J. BIOMEDICALS RESEARCH, 54: 445–453, Published online, 4 Dec. 2000. Then, through researches on application of the composite to artificial vertebrae, the inventors has found a 3-dimensional structure of an artificial vertebra having a bone-marrow regeneration ability which is achieved by using a HAp/Col composite material, and developed a biodecomposable/bioabsorbable support suitable for use with the artificial vertebra to fix it to a vertebral body.

The artificial vertebra of the present invention is made of a bioabsorbable material which has an adequate strength capable of withstanding an initial load, or a load to be applied in the early stage after implantation, and excellent abilities of bone conduction, cell differentiation/proliferation, bone-marrow formation and self-organization (bone-tissue regeneration), and exhibits excellent characteristics equivalent to an autologous bone.

Specifically, the present invention provides an artificial vertebra having a bone-marrow regenerating function and being transformable to an autologous bone, comprising a hydroxyapatite (HAp)/collagen (Col) composite body formed by pressure-dehydrating a coprecipitate of hydroxyapatite and collagen to have the weight ratio of HAp to Col ranging from 70:30 to 80:20 which is equivalent to that of a bone, and a nanocomposite structure in which HAp particles are conjugated along a Col fiber while aligned each of the c-axes of the HAp particles along the Col fiber. The HAp/Col composite body is formed with a perforated aperture for allowing a blood vessel and an osteogenic cell to intrude thereinto. The aperture is perforated in the frontward/rearward direction and rightward/leftward direction relative to the front side of a human body in a configuration analogous to that of a Volkmann's canal, wherein a plural number of the apertures are arranged at even intervals.

If HAp is excessively included beyond the weight ratio of HAp to Col in the HAp/Col composite body in the range of 70:30 to 80:20 which is equivalent to that of a bone, the HAp/Col composite body becomes brittle due to increased Young's modulus. If Col is excessively included beyond the above range, the HAp/Col composite body will have deteriorated strength.

The coprecipitate may have a cross-linked surface.

The HAp/Col composite body may be formed as a block having a horseshoe shape in a section orthogonal to the long axis thereof. In this case, a portion of the block to be located frontward relative to the front side of a human body may have a curved surface having an analogous shape to that of a vertebral body, and a portion of the block to be inserted into vertebral bodies may have rectangular planer surfaces to provide an increased contact area with the vertebral bodies.

The aperture may be perforated in the direction of the long axis of the HAp/Col composite body in a configuration analogous to that of a Haversian canal. In this case, a plural number of the apertures are arranged at even intervals.

The HAp/Col composite body may be adapted to receive a load in an early stage after implantation in cooperation with a polylactic acid plate. In this case, the HAp/Col composite body has a function of being transformed into an autologous bone in such a manner that new bone (bone marrow) is initially formed in the perforated aperture and the transformation is then extended from the new bone region to the periphery thereof.

The artificial vertebra of the present invention may include an osteogenic factor impregnated into the HAp/Col composite body.

The present invention also provides an aritifical vertebra assembly comprising in combination the above artificial vertebra, and a biodecomposable/bioabsorbable support for fixing an artificial vertebra, comprising a polylactic acid plate prepared by injection-molding molten polylactic acid and then extrusion-molding said injection-molded polylactic acid in such a manner that it is draw-oriented in a uniaxial direction, wherein the plate has four corner regions each formed with a screw hole for fixing the plate to vertebral bodies.

Further, the present invention provides an artificial vertebra assembly comprising in combination the above artificial vertebra and the above biodecomposable/bioabsorbable support, wherein the screw hole is perforated in the four corner regions of the plate in an oblique direction.

A cortical bone has an extremely high hardness. In big animals, the cortical bone is composed of a number of lamellas. Blood vessels and nerves are distributed within the cortical bone, specifically, in a Haversian canal extending along the center of the concentric lamellas and a perforating canal (Volkmann's canal) extending transversely through the lamellas.

The artificial vertebra of the present invention comprises the HAp/Col composite body formed with perforated apertures analogous to the Haversian canal and the Volkmann's canal. The characteristics of the HAp/Col composite body and the perforated apertures allows blood vessels and osteogenic cells to readily intrude in the inside of the artificial vertebra after implantation, to form a structure equivalent to that of a natural bone having a cancellous bone (bone marrow) in the central region thereof and a cortical bone (HAp/Col) surrounding the cancellous bone.

The plurality of Volkmann's canal-like apertures perforated in the frontward/rearward direction and rightward/leftward direction of the block relative to the front side of a human body have a function of allowing blood vessels to intrude from the periosteum of a vertebral body into the block together with osteogenic cells. Preferably, the aperture has a diameter of about 0.4 to 0.6 mm.

If the diameter is greater than 0.6 mm, the block is liable to cause cracks. If the diameter is less than 0.4 mm, the amount of new bone formation will be reduced, and consequently the transformation of the HAp/Col composite body to an autologous bone will be undesirably delayed.

The Haversian canal-like aperture perforated in the directions of the long axis of the block has a function of allowing blood vessels to intrude from the periosteum of a vertebral body into the block together with osteogenic cells. Preferably, the aperture has a diameter of about 0.4 to 0.6 mm. If the diameter is greater than 0.6 mm, the block is liable to cause cracks. If the diameter is less than 0.4 mm, the amount of new bone formation will be reduced, and consequently the transformation of the HAp/Col composite body to an autologous bone will be undesirably delayed.

In the artificial vertebra of the present invention, the HAp/Col composite body has a characteristic capable of allowing the above small aperture to be perforated therein with a driller or the like, and maintaining adequate flexural strength, compressive strength and Young's modulus required as an artificial vertebra even if a number of the apertures are perforated therein.

In use of the artificial vertebra of the present invention, the block is inserted into a space formed by cutting a specific vertebral body while pulling a pair of vertebral bodies located on the upper and lower sides of the specific vertebral body upward and downward to allow the upper and lower surfaces of the block to be interposed or clamped between the upper and lower vertebral body. Thus, the block or the HAp/Col composite body can receive a vertical initial load by itself as a substitute for a cortical bone, and the perforated apertures can induce the intrusion of blood vessels and osteogenic cells. If the HAp/Col is impregnated with rhBMP, bone formation will be facilitated to provide an enhanced initial strength after implantation. Over the years, the HAp/Col composite body will be transformed into an autologous bone in such a manner that new bone (bone marrow) is initially formed in each of the perforated apertures and the transformation is then extended from the new bone region to the periphery thereof.

The artificial vertebra of the present invention has the following features:

(1) After implantation, the artificial vertebra is transformed to have a structure comprising a bone marrow (new bone created in the Haversian canal-like and Volkmann's canal-like perforated apertures) and a cortical bone (bone formed by the HAp/Col composite body and the BMP impregnated therein, which is equivalent to a natural bone (natural vertebral body);

(2) A bone-remodeling unit is formed in the HAp/Col composite body corresponding to a cortical bone forms, to allow the HAp/Col composite body to be transformed into an autologous bone or to self-organize; and (3) The BMP can be absorbed directly into the HAp/Col composite body without using any other carrier.

There has not been known any artificial material capable of forming a bone-remodeling unit therein, and thus the artificial vertebra of the present invention is a novel biomedical material having a bone-conduction ability equivalent to that of an allogeneic bone.

In the present invention, the polylactic acid (PLLA) plate for use in fixing the above artificial vertebra has a mechanical characteristic and configuration suitable for anterior fusion of the cervical spine.

In view of the chemical composition, a bone is made of "protein consisting of collagen" and "inorganic crystal analogous to hydroxyapatite". The weight ratio of the protein to the inorganic crystal is about 3:7. The two materials are characteristically arranged in order even in the nano range. The collagen has a size of 300 nm, and the apatite crystal has a size of 50 nm. Thus, it can be said that a bone is a typical organic/inorganic nanocomposite.

A bone is regenerated by an osteoblast, and absorbed by an osteoclast. The metabolism of calcium and phosphorous in a lining body is widely associated with bone formation. However, in a local viewpoint, an osteoblast first synthesizes collagen, and extracellularly releases the collagen to form an organic skeleton. Then, a small apatite crystal is formed, and a bone will be developed. As above, a bone is an extracellular matrix in which apatite and collagen are autonomously conjugated together in a local space around the osteoblast. Thus, it is expected that apatite and collagen are self-organizingly conjugated together by duplicating a chemical circumstance analogous to the local space around the osteoblast.

A HAp/Col composite as a material of the artificial vertebra of the present invention is synthesized by simultaneously dropping a calcium-hydroxide suspension and a phosphoric-acid solution containing collagen into distilled water to form a coprecipitate, and pressure-dehydrating and shaping the obtained coprecipitate. During the coprecipitation or after the shaping of the coprecipitate, the surface of the coprecipitate may be cross-linked through a chemical cross-linking method using glutalaldehyde, or any other suitable cross-linking method such as a thermal cross-linking method or an ultraviolet cross-linking method, to provide an enhanced initial strength.

The HAp/Col composite synthesized through the above process has a nanocomposite structure analogous to that of a bone, in which HAp crystals are conjugated along a Col fiber while aligned each of the c-axes of the HAp particles along the Col fiber. Thus, when the HAp/Col composite body is implanted in a living body, it will be transformed into an autologous bone in a similar process to that of a natural bone. FIG. 4 is a TEM image and an electron diffraction image of the HAp/Col composite body. The images show HAp crystals arranged along a collagen fiber. The arrow in the electron diffraction image indicates the c-axis orientation of the HAp crystal.

In the artificial vertebra of the present invention, the HAp/Col composite body has a compressive strength capable of withstanding a load in an early stage after implantation. While the HAp/Col composite body is a bulk material, the surface of the HAp/Col composite body will be gradually decomposed and absorbed in vertebral bodies in contact therewith under load in a living body. In response to the absorption, macrophages are mobilized to treat the decomposition product, so that the decomposition product is differentiated into osteoclasts in the vertebral bodies. Further, the decomposition product attracts the osteoclasts, and the osteoclasts induce osteoblasts to form new bone so as to provide excellent bone conduction ability. Differently from hydroxyapatite, AW glass or lactic-acid-based polymer, the HAp/Col composite body in the artificial vertebra of the present invention is transformed into real bone in a living body.

If the HAp/Col composite body is not cross-linked, it will be absorbed by an osteoclast-like multinucleate to form a structure (pits or depressions) analogous to Howship's lacunae. It can be observed that osteoblasts positively form new bone around the structure. Thus, it is believed that the HAp/Col composite body in the artificial vertebra of the present invention can be incorporated into a bone-regeneration/absorption metabolism (remodeling cycle) to form new bone.

Any cross-linking treatment has no negative affect on the biocompatibility of the HAp/Col composite body. The cross-linking treatment provides an extended time-period allowing the HAp/Col composite body to be absorbed in a lining body. The cross-linking treatment has no affect on the function of allowing tissues to intrude in the perforated aperture, and thus the bone-conduction ability is adequately maintained. If the degree of cross-linking is increased, deterioration in cell activity will be observed. The cell activity would be deteriorated by reason that the decomposition of collagenase is not adequately developed due to the cross-linking, and consequently the absorption of the decomposition product by cells is delayed.

Both collagen and hydroxyapatite have a high affinity with protein, and the hydroxyapatite of the HAp/Col composite body used in the artificial vertebra of the present invention is a microcrystal. Thus, the HAp/Col composite body has an effective area for absorbing protein, incomparably lager than that of the conventional material using hydroxyapatite, and serves as an excellent carrier of an osteogenic factor such as rhBMP. The impregnation of the osteogenic factor such as rhBMP facilitates bone formation in the entire peripheral surface of the artificial vertebra to allow a load to be imposed on the artificial vertebra in earlier stage after implantation. In addition, the artificial vertebra is quickly integrated with the natural vertebra bodies. Thus, the artificial vertebra of the present invention can be used to achieve desirably reduced treatment period.

The artificial-vertebra fixing support of the present invention comprising a polylactic acid (PLLA) plate may be produced by forming a flat plate with molten polylactic acid through injection molding, setting the flat plate in a vessel of an extrusion machine, and forcedly extruding the flat plate from a die of the extrusion machine while heating the vessel.

The PLLA plate for fixing the artificial vertebra of the present invention keeps its original configuration for at least 24 weeks after it is implanted in a living body. The PLLA plate should be gradually decomposed to prevent surrounding cells from being damaged due to the acidification of pH caused when the plate is decomposed and absorbed in a living body. From this point of view, the PLLA plate of the present invention is a desirable material.

The PLLA plate of the present invention has a sufficient strength to prevent the artificial vertebra from dropping off after implantation and firmly join to a vertebral body serving as an implant bed. Particularly in anterior fusion of the human cervical spine receiving a vertical load, a plate for supporting an artificial vertebra implanted in a cervical vertebral body is essentially required to have a high strength. The PLLA plate of the present invention has a sufficient strength capable of withstanding such a load. In addition, the PLLA plate is superior to a metal plate in that the time-period allowing the plate to be absorbed in a living body can be controlled by adjusting its production conditions.

When the artificial vertebra of the present invention is implanted under the skin, the surface of the HAp/Col composite body is segmentalized by the infiltration of phagocytes, and the segmentation will continue even after 24 weeks. The infiltration of phagocytes is considered as the same reaction as that to be caused after implantation of a collagen sponge or a collagen membrane. This reaction is different from a rejection symptom in that it involves neither the mobilization of granulocyte nor the emergence of lymphocyte.

According to a test in which a peg is inserted into an aperture perforated in a radius/ulna of a dog, an HE-stained sample of the HAp/Col composite body implanted in the aperture suggests that the HAp/Col composite body can be joined directly to a bone. A transformation zone observed in the boundary region between the HAp/Col composite body and a new bone in a Villanueva-stained sample is considered as a portion of the surface of the HAp/Col composite body in which HAp is deposited.

The phenomenons that osteoclasts emerge in the Howship's lacunae-like structure formed in the surface of the HAp/Col composite body and that osteoblasts are arranged in the boundary region between the HAp/Col composite body and a new bone could be enzyme-histochemically proved. Thus, it is believed that the HAp/Col composite body is an excellent biomedical material capable of inducing osteogenic cells to form a bone-remodeling unit.

BRIEF DESCRIPTION OF THE DRAWINGS

FIG. 1 shows the configuration of an artificial vertebra for humans in Example-1 of the present invention, wherein FIG. 1(a) is a top plan view, FIG. 1(b) being a front view, and FIG. 1(c) being a side view.

FIG. 5 shows the configuration of an artificial vertebra in Example-3, wherein FIG. 5(a) is a top plan view, and FIG. 5(b) is a side view.

DESCRIPTION OF THE PREFERRED EMBODIMENT

Figure 1:
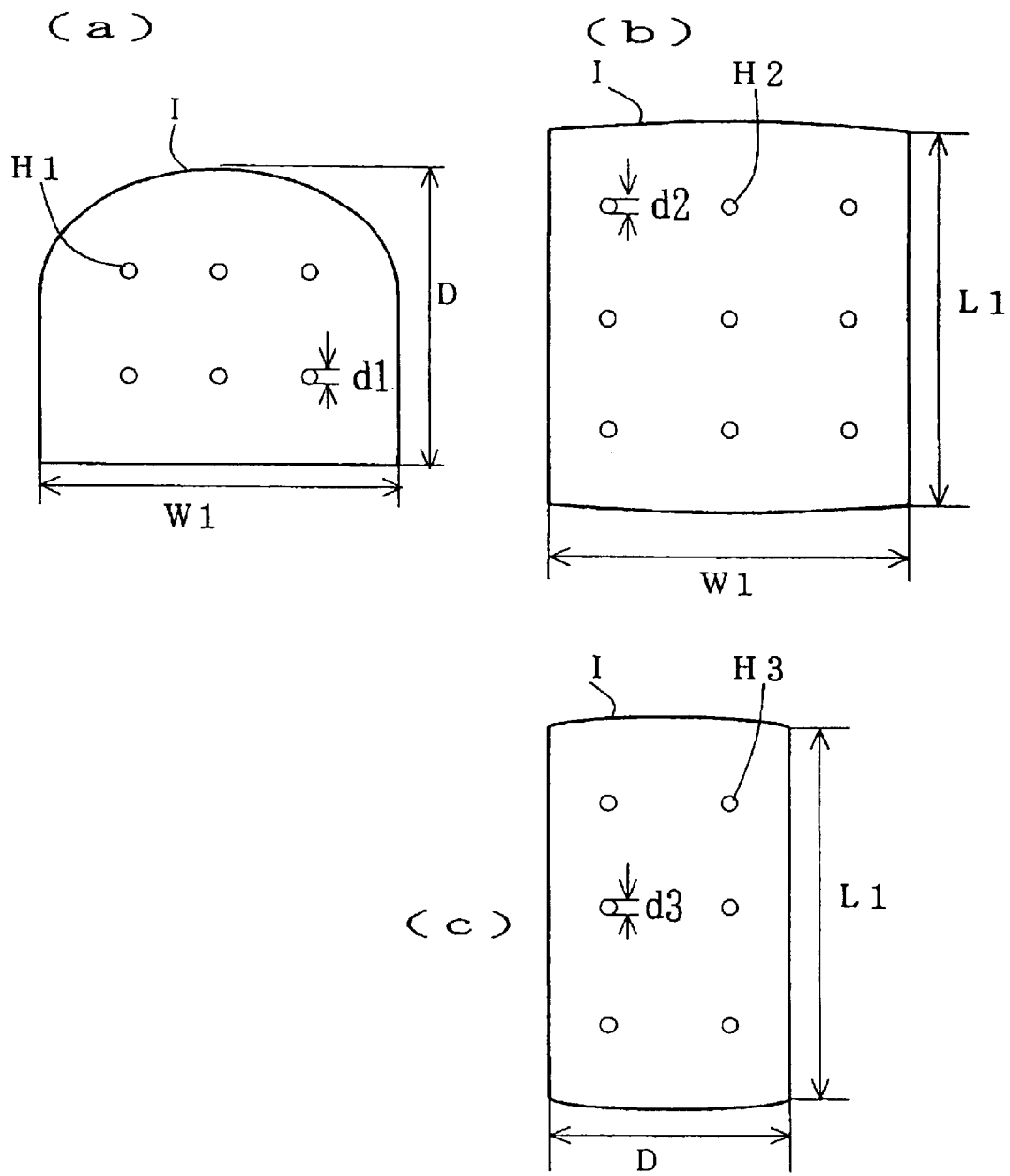

An artificial vertebra of the present invention comprises a hydroxyapatite (HAp)/collagen (Col) composite body. In production of the HAp/Col composite body, a calcium-hydroxide suspension and a phosphoric-acid solution including collagen are first prepared, and the two solutions are simultaneously dropped into a reaction chamber containing distilled water by using a tube pump to form a coprecipitate or synthesize a HAp/Col composite. Then, the obtained coprecipitate is filtered and rinsed. At this stage, the percentage of water content is in the range of about 5 to 50%. The coprecipitate is pressure-dehydrated through a cold isostatic pressing (CIP) method, preferably at pH 8, at a temperature of 40° C. under a pressure of 200 MPa. As a result, a HAp/Col composite body having a submicron-order pore size and a porosity ranging from about 10 to 68% depending on the percentage of water content is obtained.

In the obtained HAp/Col composite body, a primary particle size (approximately equal to a crystallite size) of HAp is about 50 nm, and a secondary particle (a fibrous composite) has a maximum length of about 20 μm and a width of about 0.5 to 1 μm, on average. The HAp/Col composite body can be arranged to have a three-point flexural strength of about 38 to 45 MPa, and a Young's modulus of about 2 to 3 GPa. The Young's modulus of living bone is varied depending on regions, and distributed in the range of 4 to 30 GPa. Optimally, the HAp/Col composite body should have a Young's modulus approximate to that of natural bone. While a conventional ceramics is brittle and fractural due to its extremely high Young's modulus, the HAp/Col composite body can be readily prepared to have various Young's moduluses ranging from that of a soft living bone to a hard living bone. A higher Young's modulus provides higher brittleness, and a smatter Young's modulus provides higher softness. If a chemical cross-linking method is performed to introduce a cross-link in collagen simultaneously with the coprecipitation in the process of synthesizing the HAp/Col composite, the following method may be preferably used. It is understood that the cross-linking method for use in the present invention is not limited to the chemical cross-linking method, but any other suitable cross-linking method such as a thermal cross-linking or ultraviolet cross-linking method may be used.

In a cross-linking method using glutalaldehyde (GA), GA is first added into the $Ca(OH)_2$ suspension (at a concentration of 1 wt % relative to collagen). The color of the sample is changed to yellow by adding GA. During the simultaneous dropping process, a cross-linking reaction to collagen is caused by GA before a self-organizing structure of collagen and apatite is stably established.

Specifically, the formation of the self-organizing structure would be hindered by reason that the reaction between GA and a lysine residue serving as a cross-linking point in collagen takes precedence. While no addition of GA causes the phenomenon that decalcified collagen is dispersed over the phosphoric-acid solution, the addition of GA allows the decalcified collagen to be agglutinated in the phosphoric-acid solution or even in a hydrochloric-acid solution, without dispersion. Considering this phenomenon, it is believed that the addition of GA causes introduction of cross-link in collagen of the composite, and the cross-linked collagen gives rise to the coloring of the sample.

According to a transmission electron microscope image of a HAp/Col composite with a nanostructure synthesized by adding GA, a fibrous structure is macroscopically observed. In microscopical observation, a number of short fibers each formed of a composite of apatite and collagen are connected with each other to form a membranous structure. As apparent from this image, the cross-linking treatment suppresses the formation of the self-organizing structure in which apatite crystals are conjugated onto a collagen fiber even under a suitable condition for the self-organization of the HAp/Col composite.

The respective amounts of water and collagen in the HAp/Col composite body are determined through thermal analysis. The HAp/Col composite body subjected to a cross-linking treatment can have enhanced flexural strength, specifically a maximum flexural strength of 60 MPa. The cross-linking treatment using GA improves a material defect such that the surface of the HAp/Col composite body is swelled in a short time-period to provide enhanced material stability and improved operationality of the artificial vertebra during implantation.

When it is required to accelerate early bone formation because the artificial vertebra is implanted in a load-bearing region, a method of impregnating the HAp/Col composite body with rhBPM-2 may be effectively used. In this case, the concentration of rhBPM-2 is preferably 400 μg/ml or more.

If the artificial vertebra is used for humans, the HAp/Col composite body is formed as a block, for example, having a horseshoe shape in a section orthogonal to the long axis thereof. Preferably, a portion of the block to be located frontward relative to the front side of a human body has a curved surface, and a portion of the block to be inserted into vertebral bodies has rectangular planer surfaces to provide an increased contact area with the vertebral bodies. For this purpose, the HAp/Col composite body may be shaped as shown in FIG. 1 by using a computer controlled drilling machine. Several HAp/Col composite bodies may be prepared to have a width W1 of about 15 mm, a depth D of about 10 mm, and a length L1 of 10 to 40 mm, wherein each of the HAp/Col composite bodies has a different length by 5 mm.

Then, a Haversian canal-like aperture having a diameter of about 0.5 mm was perforated in the direction of the long axis of the block using a drilling machine. As shown in FIG. 1, a plural number of the apertures are arranged at even intervals in cross-section. Further, a plurality of Volkmann's canal-like apertures each having a diameter of about 0.5 mm are perforated in the frontward/rearward direction and rightward/leftward direction of the block. Preferably, the number of these apertures is arranged as much as possible depending on the strength of the HAp/Col composite body.

Generally, a flat plate produced simply by injection-molding polylactic acid (PLLA) has mechanical characteristics, such as a flexural strength of about 77 MPa, a flexural modulus of about 3.3 Gpa, and a tensile strength of about 67 MPa. A published flexural strength of cortical bone is in the range of 100 to 200 MPa. Thus, considering the strength reduction due to hydrolysis in a living body, the injection-molded PLLA plate has an insufficient mechanical strength as a support for fixing an artificial vertebra.

While an injection-molded piece can be extended through a rolling process to improved strength, the diameter of the piece is more reduced as the draw ratio is increased, and a final product will be hardly machined. Otherwise, an injection-molded plat plate can be extrusion-molded in such a manner that molecules are crystallized while orienting in a uniaxial direction, to provide enhanced mechanical characteristics at approximately double value, specifically a flexural strength of about 180 MPa, and a flexural modulus of about 6 Gpa. A flexural strength test herein was performed according to JISK-71717. Preferably, the PLLA plate has four corner regions each formed with a screw-insertion hole perforated in an oblique direction to prevent a screw screwed into a vertebral body from loosening and escaping.

PRODUCTION EXAMPLE-1

(Production Example of HAp/Col Composite Body)

199.1 mmol of calcium hydroxide was added into 2 $dm^3$ of distilled water, and the solution was stirred to keep it as a homogeneous suspension. 59.7 mM of phosphoric-acid solution including 5 g of pig-skin-derived atelocollagen was also prepared. These two solutions were simultaneously dropped into a reaction vessel containing 1 dm³ of distilled water by using a tube pump. In this synthesizing process, the mixed solution in the reaction vessel was controlled at pH 8 by a pH controller. Further, the temperature of the mixed solution was controlled at 40° C. while immersing the reaction vessel into a water bath. A formed precipitate was filtered through a glass filter and rinsed. Then, the precipitate was pressure-dehydrated under 200 MPa for 15 hours through a CIP method to form a HAp/Col composite body.

The HAp/Col composite body in the form of a block had a water content of about 10% and a porosity of about 20%, and the weight ratio of HAp to collagen was 80/20 (wt %). The block was immersed into and dispersed over distilled water, and then the dispersed composite was scooped on a micro-grid covered by a collodion film to prepare a sample for a transmission electron microscope (TEM). After electron microscope observation, the sample was subjected to electron diffraction. The pH and temperature in the synthesizing process could be controlled to allow the HAp/Col composite body to have a nanocomposite structure analogous to that of natural bone, in which HAp is localized around a collagen fiber while aligned the c-axis of HAp orients along a Col fiber having a length ranging from several μm to 10 μm.

The HAp/Col composite body was cut into a block of 20×5×3 mm³, and the block was subjected to a three-point flexural test under the conditions of a crosshead speed of 0.5 mm/min, and a span of 15 mm. In this test result, a three-point flexural strength was 39.5±0.88 MPa, and Young's modulus was 2.5±0.38 GPa.

Test Example-1

(Biocompatibility Test of HAp/Col Composite Body)

The HAp/Col composite body produced in the above Production Example was cut into blocks as samples each having a size of 4×4×1 mm³, and implanted in the dorsal regions of fifteen Wister rats, respectively. After 2, 4, 8, 12 and 24 weeks since implantation, the implanted samples were extracted. Each of the extracted samples was cut into two exact halves. One was used as a toluidine-blue-stained sample for an optical microscope and a sample for a TEM, and the other was used as a sample for a scanning electron microscope (SEM). The peripheral surface of the HAp/Col composite block after 2 to 4 weeks since implantation was infiltrated with a number of cells each having a round nuclei.

After 4 weeks, the surface of the HAp/Col composite block was segmented, and fibrous tissues intruded into cracks created in the segmented surface. From the TEM observation, it was confirmed that these cell are phagocytes phagocytizing the debris of the HAp/Col composite block. The peripheral surface of the HAp/Col composite block included a small number of fibroblasts. After 12 weeks, the peripheral surface of the HAp/Col composite block was formed with a number of new blood vessels. Even after 24 weeks, the HAp/Col composite block was kept in a block shape, and phagocytes were still observed therein while the number thereof was reduced as compared to that at the early stage after implantation.

Test Example-2

(Evaluation on Bone-Conduction Ability of HAp/Col Composite Body)

A bullet-shaped block (5×5×10 mm³), so-called peg, comprising the HAp/Col composite body was prepared, and each of the surfaces of the block was formed with four drilled apertures each having a diameter of 0.5 mm. Then, three of the block were immersed, respectively, into rhBPM-2 solutions of 0 μg/ml, 200 μg/ml and 400 μg/ml, and deaerated with a reversed air pump to allow the respective solutions to be completely impregnated therein.

These three kinds of blocks different in impregnated rhBMP amount were implanted, respectively, in three apertures of 6 mm diameter drilled in the bilateral radiuses or ulnas of each of five beagles at even intervals. As a comparative example, three apertures were simply drilled in the radiuses or ulnas of another one beagle.

X-ray photographs were taken from three beagles including the comparative example weekly for 12 weeks after implantation to compare respective time-periods required for concrescence of the block to the bone. The blocks were extracted from two beagles after 8 weeks since implantation, and from four beagles including the comparative example after 12 weeks, to prepare 1) decalcified HE-stained samples, 2) ALP, TRAP enzyme histochemistry, and 3) non-decalcified Villanueva-stained samples. Optical microscope photographs were also taken from the HE-stained samples prepared after 12 weeks to measure the occupation ratio (% bone area) of new bone created on the surface of the composite block by using Macintosh computer software (NIH image). Further, the thickness of the new bone created on the surface of the composite block was measured at three points, and the average value of the measured thicknesses was determined.

In the group of the blocks using rhBMP, callus was formed after two weeks since implantation in all cases. In the group of the blocks using no rhBMP, the formation of callus was poor, but observed after 4 weeks since implantation in all cases. It was judged that synostosis is achieved on X-ray photographs when any radiolucent image in the boundary region between the peg and the bone disappears, and the shading is homogenized. The synostosis in the group of the blocks having the impregnated rhBMP of 400 μg/ml was achieved significantly earlier than the group of 0 μg/ml. After 8 weeks since implantation, the composite block was joined directly to new bone having a secondary osteon (Haversian system), and non-calcified regions were scattered. A resorption-lacunae-like structure was formed on the surface of the composite block, and multinucleates were observed thereon. Spindle-shaped cells are arranged in the boundary region between the composite block and the bone. According to Villanueva staining, the presence of a transformation zone was found between new bone and the composite block. A number of cells existed on the side of the new bone in the transformation zone.

The spindle-shaped cells were positively stained by ALP staining. This suggests that these cells are osteoblasts. Not only multinucleates in the resorption lacunae existing in the secondary osteon (Haversian system) but also multinucleates in the resorption-lacunae-like structure formed in the transformation zone were positively stained by TRAP staining. This suggests that these cells are osteoclasts. While no significant difference in the occupation ratio (% bone area) of new bone was confirmed between the composite blocks, the new bone was formed in the surfaces of the composite blocks having the impregnated rhBMP of 400 μg/ml at a thickness significantly greater than that in the surfaces of the composite blocks of 0 μg/ml.

The HAp/Col composite block had a bone-like structure in which each of the c-axes of HAp crystals aligned along a collagen fiber. The HAp/Col composite block implanted under the skin was segmented, and infiltrated with macrophages for phagocytizing the segmented composite. The HE-stained sample of the HAp/Col composite block implanted in the aperture of the bone suggests that the HAp/Col composite body can be joined direct to natural bone. The phenomenons that osteoclasts emerge in the Howship's lacunae-like structure created in the surface the HAp/Col composite body and that that osteoblasts are arranged in the boundary region between the HAp/Col composite body and a new bone could be enzyme-histochemically proved.

In the test where the HAp/Col composite blocks were implanted in the apertures of the bone, the time-period required for synostosis in the group of 400 µg/ml was significantly shorter than that in the group of 0 µg/ml, and new bone was significantly thickly formed in the surfaces of the HAp/Col composite blocks. While the group of 400 µg/ml shows a tendency to have a higher occupation ratio (% bone area) of new bone than that of other groups, there was no significant difference between the group of 0 µg/ml and the group of 200 µg/ml.

Test Example-3

(Evaluation on Influence of BMP Impregnation in Implanting in Load-Bearing Region)

In a long-tube-shaped implant formed of the HAp/Col composite to filling a bone-defect area, the influence of the presence of the impregnated BMP in the implant implanted in a load-bearing region on the connection in the boundary with bone and the bone-conduction/induction was comparatively studied.

The HAp/Col composite body produced in Production Example-1 was subjected to a surface cross-linking treatment using glutalaldehyde to prepare a tibia implant. The HAp/Col composite body used for the implant was increased in cross-link number and improved in orientation of collagen to have an enhanced three-point flexural strength of 60 MPa.

Figure 5:
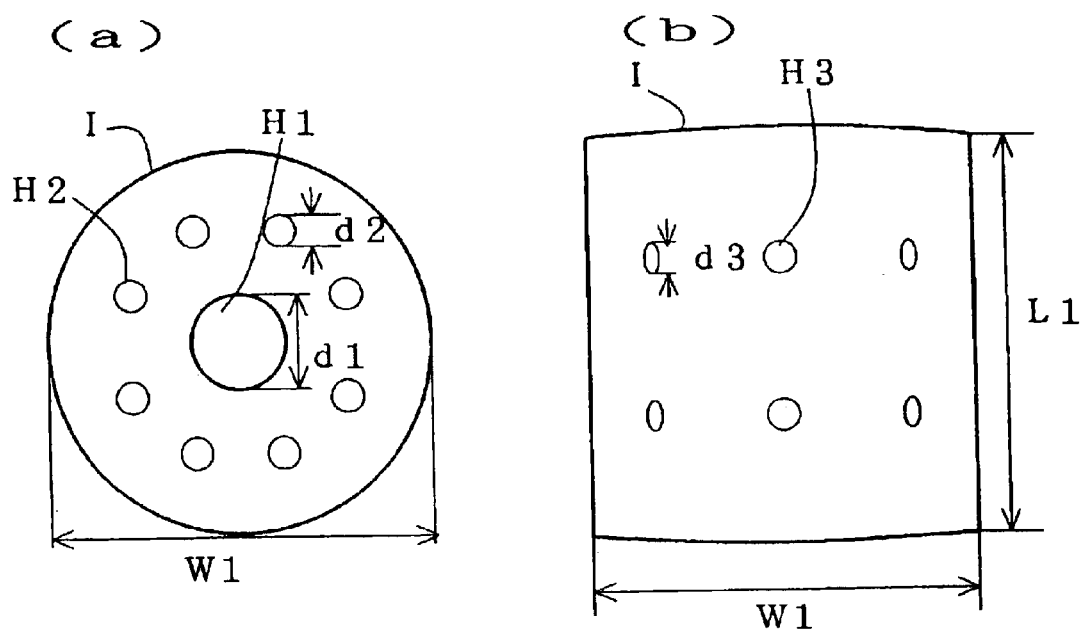

As shown in FIG. 5, one aperture H1 having a diameter d1 of 3 mm was drilled at the center in the long axis of the columnar implant I having a diameter W1 of 15 mm and a length L1 of 20 mm, and eight apertures H2 each having a diameter d2 of 1 mm were drilled radially around the aperture H1. Twelve apertures each having a diameter d3 of 1 mm were also drilled from the side surface of the implant I. The implant was implanted in the right tibia of each of three beagles. Further, the implant was impregnated with 400 µg/ml of BMP under a negative pressure, and this implant was implanted in the right tibia of each of two beagles. The periosteum around the implant was completely removed, and the implant was fixed to the tibia using an Ilizarov external fixator.

After 12 weeks, a sample was collected from one of the beagles in each of the BMP(+) group and the BMP (−) group. The external fixators of two beagles in the BMP(+) group were removed after 12 weeks to fully apply a load to the implants of the two beagles. After 24 weeks, a sample was collected from each of the two beagles.

A load was applied to the BMP (−) group under the fixture using the external fixator, and a sample was collected after 18 and 24 weeks. After implantation, X-ray photographs were taken to determine the status of bone-formation/synostosis. Respective bone densities before implantation and at sampling were also measured through a DXA method to compare the amount of bone formation around the implant. Decalcified HE-stained samples and Villanueva-stained samples were prepared from the collected samples to observe the connection with the bone in the boundary region between the implant and the bone and measure the amount of new bone created in the drilled apertures of the implant.

The average value of BMD was 2.596±0.099 g/cm$^2$ before implantation, 2.551 g/cm$^2$ in the BMP (−) group after 12 weeks, 2.566 g/cm$^2$ in the BMP (+) group after 12 weeks, 2.335 g/cm$^2$ in the BMP (−) group after 24 weeks, and 2.186 g/cm$^2$ in the BMP (+) group after 24 weeks.

On X-ray photographs, while the BMP (−) group was poor in callus formation around the implant, synostosis was achieved in the boundary region between the implant and the bone at least after 12 weeks. In bone-cut samples, the boundary region between the implant and the bone also coalesced completely after 12 weeks. However, while some implants exhibited the segmentation of the HAp/Col composite body and the bone formation in the central region thereof, other implants were kept in the original configuration at implantation. According to the HE and Villanueva-stained samples, the HAp/Col composite body was joined directly to new bone. Further, a resorption-lacunae-like structure was formed to extend to the inside of the implant.

In the surface of the composite body, multinucleates were observed at the resorption-lacunae formed in the boundary region between the implant and the bone, and spindle-shaped cells were arranged on the surface of the bone. This shows that the HAp/Col composite body takes a bone connection form analogous to a bone-remodeling unit in which osteoclasts absorb the composite body, and osteoblasts add new bone. As seen in the phenomenon that a cartilage column was formed depending on regions, a bore formation form considered as endochondral ossification was also observed In the BMP (+) group on X-ray photographs, callus was formed to wrap around the entire peripheral surface of the implant. After 12 weeks, the HAp/Col composite body completely coalesced with the bone, and a medullary cavity was formed. The HAp/Col composite body was left in an island shape on the outside of cortical bone. After 24 weeks, the maturation of the new bone was observed from the tendency of reduction in external calcification and the highlighted image of hardening in the cortical bone region.

In bone-cut samples, the segmented HAp/Col composite bodies were left in an island shape within the cortical bone. After 24, a matured bone was formed in the inside of the implant as well as the entire peripheral surface thereof. A medullary-cavity-like structure was observed in the central region of the implant. In tissue samples, it was verified that the HAp/Col composite body is joined directly to natural bone. The formation of cartilage column was observer only at a part of the implant.

Test Example-4

(Implantation in Cervical Spine of Dog)

The HAp/Col composite body produced in Production Example-1 was shaped into a block of 5×5×10 mm$^3$. Under a negative pressure, one group of non-cross-linked artificial vertebrae were impregnated with 0 µg/ml of BMP (hereinafter referred to as "0 µg/ml group"), and the other group of non-cross-linked artificial vertebrae were impregnated with 400 µg/ml of BMP(hereinafter referred to as "400 µg/ml group"). A PLLA plate for use in preventing escape of the artificial vertebrae was fixed with titanium screws. Two apertures were drilled, respectively, at distal and proximal positions of the plate, and the screws are inserted into the corresponding apertures in an oblique direction. The artificial vertebra of the 0 µg/ml group were implanted in each of eight beagles, and the artificial vertebra of the 400 µg/ml group were implanted in each of three beagles.

The cervical spine of the beagle was developed from the front of the body. Then, a groove slightly lager than the artificial vertebrae was cut between C3 and C4, or C4 and C5 to perform the fusion of one intervertebra and two vertebral bodies. The periosteum on the frontward of the vertebral body was completely peeled. As with Test Example-1, the performance after implantation was evaluated in accordance with X-ray photographs and tissue observations. Samples of the 0 µg/ml group were collected from four, two and two beagles, respectively, after 12, 16 and 24 weeks. Samples of the 400 µg/ml group were collected from one, one and one beagle, respectively, after 12, 16 and 24 weeks. After implantation, X-ray photographs were taken monthly to evaluate the status of bone-formation/synostosis around the artificial vertebra. The collected samples were histologically evaluated.

According to test results, while the 0 µg/ml group was poor in callus formation, synostosis was achieved in the boundary region between the artificial vertebra and the bone at least after 12 weeks. In the 400 µg/ml group, callus was significantly formed, and callus emerged in the frontward of the artificial vertebra. After 12 weeks or more since implantation, a thick new bone was formed in the frontward of the artificial vertebra.

According to bone-cut samples, the composite body of the 0 µg/ml group was joined directly to new bone without existence of any soft tissue between the artificial vertebra and the vertebral body. The PLLA plate was kept in the original configuration. After 12 weeks, the artificial vertebra was progressively absorbed, and hardly discriminated from the surrounding vertebral bodies. In the 400 µg/ml group, a thick cortical bone was formed in the frontward of the artificial vertebra.

According to tissue samples, HE-stained samples after 12 weeks showed that the artificial vertebra is joined directly to new bone, and the observation result was fundamentally the same as that in the aforementioned implantation in tibia. In the surface of the composite body, multinucleates were observed at the resorption-lacunae formed in the boundary region between the artificial vertebra and the bone, and spindle-shaped cells were arranged on the surface of the bone to form the bone-remodeling unit.

Test Example-5

(Implantation in Cervical Spine of Monkey)

As with Test Example-4, a columnar artificial vertebra having a diameter of 4 mm and a height of 5 mm was produced, and degassed to suck rhBMP-2 (0 mg/ml, 1 mg/ml) therein. Then, the artificial vertebra was implanted between C4 and C5 of the cervical spine of each of eight Japanese monkeys, and fixed by the same PLLA plate as that in Test Example-4. X-ray photographs and CT images were taken after implantation, and samples were collected for 3 months to perform histologic evaluations as with Test Example-4. All results of image observation and tissue images were the same as those obtained in the aforementioned 0 µg/ml and 400 µg/ml groups.

Embodiment (Embodiment-1)

Figure 2:
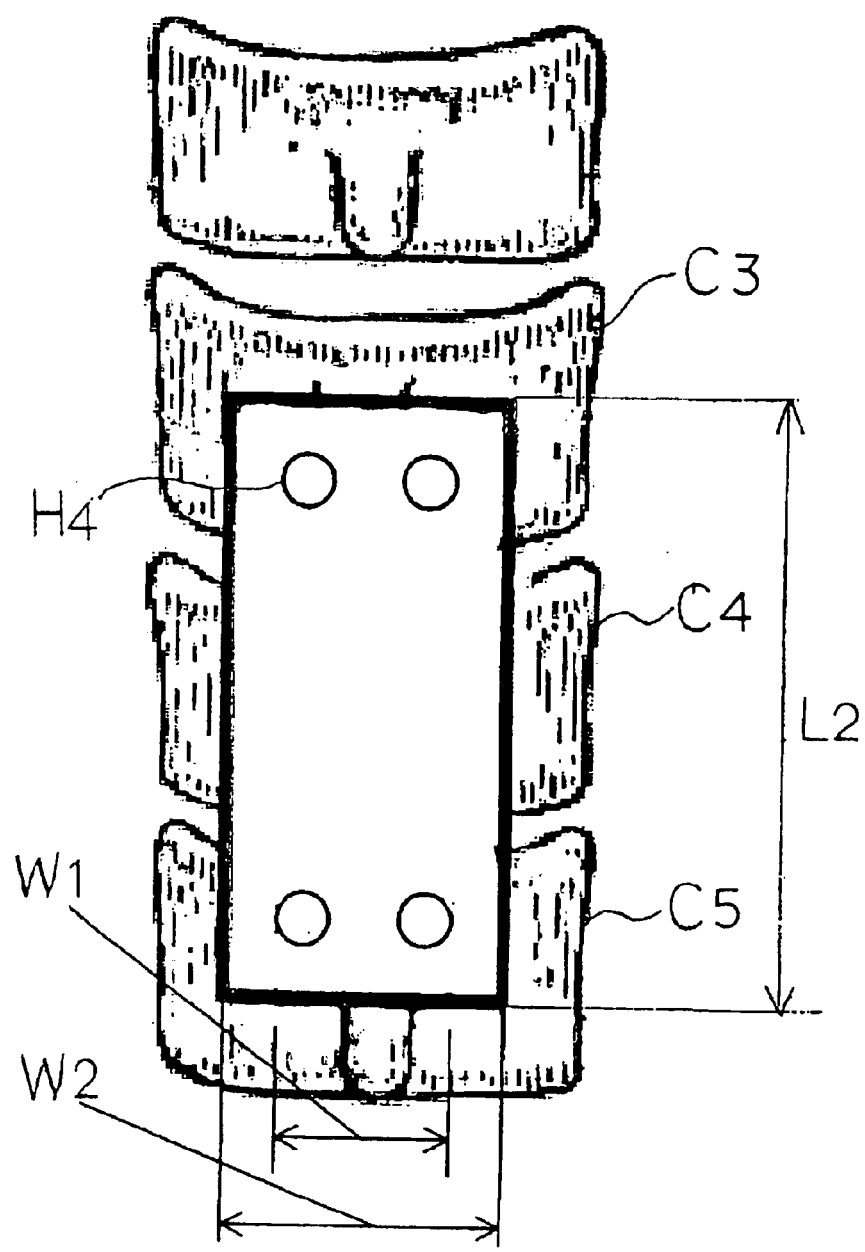
FIG. 2 is a front view showing the state after the artificial vertebra in FIG. 1 is fixed to human cervical spine by a support plate.
Figure 3:
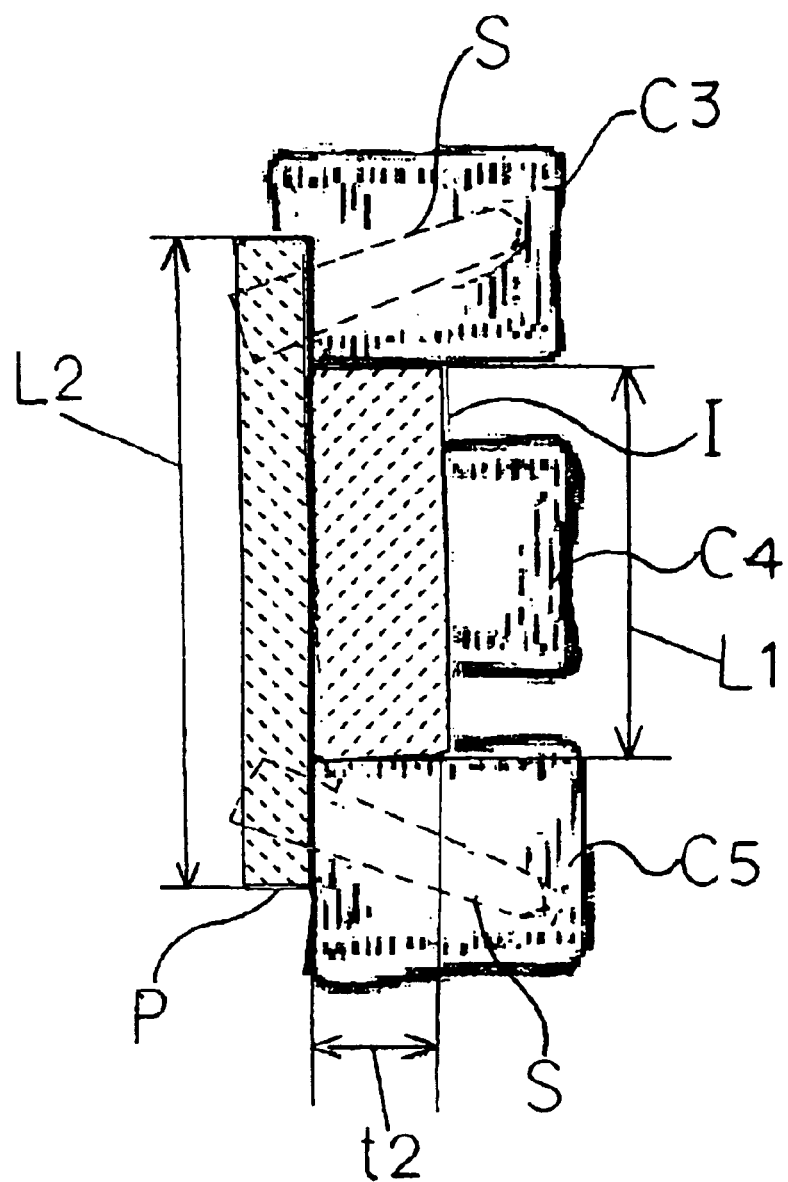
FIG. 3 is a side view showing the state after the artificial vertebra in FIG. 1 is fixed to human cervical spine by a support plate.
Figure 4:
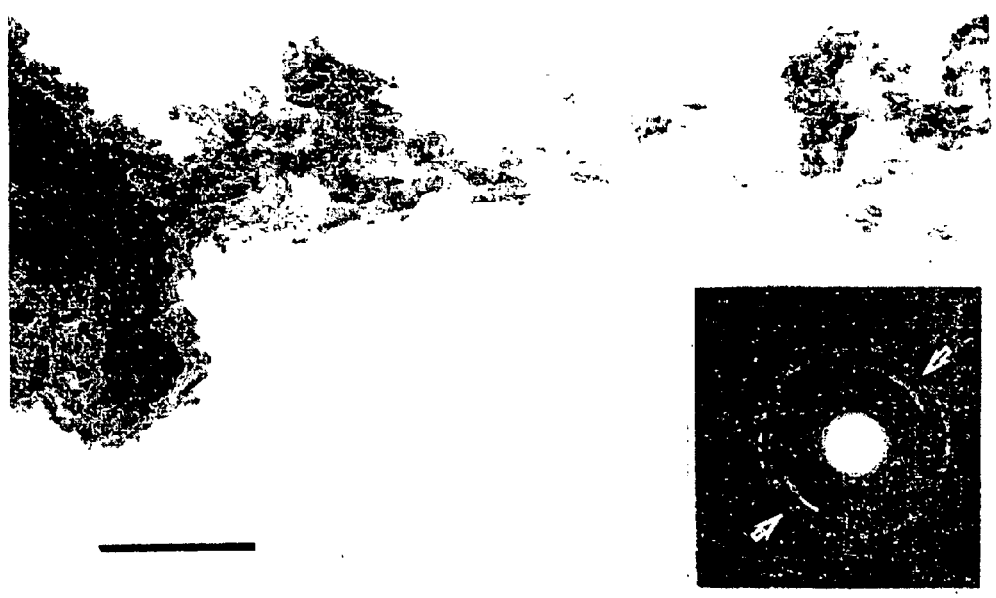
FIG. 4 is photographs showing a TEM image (scale bar: 1 μm) and an electron diffraction image of a HAp/Col composite material.

An artificial vertebra for humans was produced by using the HAp/Col composite body in Production Example-1. FIG. 1 shows the configuration of the artificial vertebra, wherein FIG. 1(a) is a top plan view, FIG. 1(b) being a front view, and FIG. 1(c) being a side view. FIG. 2 is a schematic front view showing the state after the artificial vertebra in FIG. 1 is fixed to human cervical spine by a support plate. FIG. 3 is a partial sectional side view showing the state after the artificial vertebra in FIG. 1 is fixed to human cervical spine by a support plate.

As shown in FIG. 1, a cervical-spin artificial vertebra I comprises a horseshoe-shaped block having a depth D of 10 mm, a width W1 of 15 mm, and a length L1 of 20 mm. The artificial vertebra I has six apertures each having a diameter d1 of 0.5 mm. The apertures are drilled in the long axis of the block at even intervals. Further, nine apertures H2 each having a diameter d2 of 0.5 mm are drilled in the forward/rearward direction of the block, and six apertures H3 each having a diameter d3 of 0.5 mm are drilled in the rightward/leftward direction of the block. A polylactic-acid (PLLA) support plate P for fixing the artificial vertebra is produced by injection-molding molten polylactic acid and extrusion-molding the injection-molded product in such a manner that molecules are crystallized while orienting in a uniaxial direction. The PLLA plate P has a length L2 of 25 mm, a width W2 of 10 mm and a thickness T of 2 mm. As shown in FIGS. 2 and 3, each of the four corner regions of the PLLA plate P is formed with a screw-insertion aperture H4 having a diameter of 4 mm. The aperture H4 is drilled in an oblique direction to prevent a screw S inserted therein from loosening. The screw S is made of titanium. The screw S is screwed into the vertebral bones C3 and C4 through the aperture H4 to fix the PLLA plate P and the block as shown in FIG. 3.

INDUSTRIAL APPLICABILITY

As mentioned above, the artificial vertebra of the present invention comprising a HAp/Col composite body prepared through a coprecipitation process and having a self-organizing function is a biomedical material having a bone-remodeling unit and a bone-conduction ability equivalent to an allogeneic bone. The artificial vertebra added with an osteogenic factor such as BMP can form new bone in the entire peripheral surface under a load at earlier stage after implantation and accelerate the transformation of the new bone to matured bone.

There has been no report describing that an artificial vertebra implanted in the cervical spine receiving a vertical load as in dogs or monkeys. The artificial vertebra of the present invention can achieve human's cervical spine fusion using a bioabsorbable material capable of being transformed to an autologous bone. Thus, the artificial vertebra of the present invention greatly contributes to reparative surgeries for a bone defect area of a vertebral body.

What is claimed is:

1. An artificial vertebra system having a bone-marrow regenerating function and being transformable to an autologous bone, comprising a hydroxyapatite (HAp)/collagen (Col) composite body formed by pressure-dehydrating a coprecipitate of hydroxyapatite and collagen to have the weight ratio of HAp to Col ranging from 70:30 to 80:20 which is equivalent to that of a bone, and a nanocomposite structure in which HAp particles are conjugated along a Col fiber while aligned each of the c-axes of said HAp particles along said Col fiber, said HAp/Col composite body being formed with a perforated aperture for allowing a blood vessel and an osteogenic cell to intrude thereinto, said aperture being perforated in the frontward/rearward direction and rightward/leftward direction relative to the front side of a human body in a configuration analogous to that of a Volkmann's canal, wherein a plural number of said apertures are arranged at even intervals.

2. The artificial vertebra as defined in claim 1, wherein said coprecipitate has a cross-linked surface.

3. The artificial vertebra as defined in claim 1, wherein said HAp/Col composite body is formed as a block having a horseshoe shape in a section orthogonal to the long axis thereof, wherein a portion of said block to be located frontward relative to the front side of a human body has a curved surface having an analogous shape to that of a vertebral body, and a portion of said block to be inserted into vertebral bodies has rectangular planer surfaces to provide an increased contact area with the vertebral bodies.

4. The artificial vertebra as defined in claim 1, wherein said aperture is perforated in the direction of the long axis of said HAp/Col composite body in a configuration analogous to that of a Haversian canal, wherein a plural number of said apertures are arranged at even intervals.

5. The artificial vertebra as defined in claim 1, wherein said HAp/Col composite body is adapted to receive a load in an early stage after implantation in cooperation with a polylactic acid plate, wherein said HAp/Col composite body has a function of being transformed into an autologous bone in such a manner that new bone (bone marrow) is initially formed in said perforated aperture and the transformation is then extended from said new bone region to the periphery thereof.

6. The artificial vertebra as defined in claim 1, which includes an osteogenic factor impregnated into said HAp/Col composite body.

7. An artificial vertebra assembly comprising in combination the artificial vertebra as defined in claim 1, and a biodecomposable/bioabsorbable support for fixing an artificial vertebra, including a polylactic acid plate prepared by injection-molding molten polylactic acid and then extrusion-molding said injection-molded polylactic acid in such a manner that it is draw-oriented in a uniaxial direction, said plate having four corner regions each formed with a screw hole for fixing said plate to vertebral bodies.

8. An artificial vertebra assembly in combination the artificial vertebra, and the biodecomposable/bioabsorbable support as defined in claim 7, wherein said screw hole is perforated in the four corner regions of said plate in an oblique direction.

* * * * *